United States Patent [19]

Igarashi et al.

[11] Patent Number: 5,597,386

[45] Date of Patent: Jan. 28, 1997

[54] HAIR COLORING COMPOSITION COMPRISING ANTI-HAIR ANTIBODIES IMMOBILIZED ON COLORING MATERIALS, AND HAIR COLORING METHODS

[75] Inventors: Shigeru Igarashi; Toshihiro Usui, both of Odawara; Junichiro Hiraoka, Yokohama; Keiko Hashimoto; Hideyo Uchiwa, both of Odawara; Umeji Murakami, Naka-gun; Kenichi Sugimoto; Hiromi Minamino, both of Odawara; Toshio Horikoshi, Chigasaki, all of Japan

[73] Assignee: Kanebo, Ltd., Tokyo, Japan

[21] Appl. No.: 284,524

[22] PCT Filed: Dec. 8, 1993

[86] PCT No.: PCT/JP93/01780

§ 371 Date: Aug. 8, 1994

§ 102(e) Date: Aug. 8, 1994

[87] PCT Pub. No.: WO94/13253

PCT Pub. Date: Jun. 23, 1994

[30] Foreign Application Priority Data

Dec. 8, 1992 [JP] Japan .................................. 4-351971
Dec. 8, 1992 [JP] Japan .................................. 4-351973
Nov. 24, 1993 [JP] Japan .................................. 5-319141

[51] Int. Cl.$^6$ .............................. A61K 7/13; C07K 16/18
[52] U.S. Cl. .......................... 8/405; 8/401; 8/428; 8/552; 8/561; 8/563; 8/637.1; 8/930; 424/70.6; 530/387.1; 530/388.9

[58] Field of Search .................. 8/401, 405, 552, 8/563, 637.1, 602, 930, 428; 424/70, 70.6; 530/388.9, 387.1

[56] References Cited

U.S. PATENT DOCUMENTS

| | | | |
|---|---|---|---|
| 3,987,161 | 10/1976 | Widder | 424/70 |
| 4,169,137 | 9/1979 | Hirschfeld et al. | 424/8 |
| 4,373,932 | 2/1983 | Gribnau et al. | 436/501 |
| 4,780,422 | 10/1988 | Mitani et al. | 436/524 |
| 4,870,010 | 9/1989 | Hayes | 424/70 |
| 4,999,195 | 3/1991 | Hayes | 424/70 |
| 5,132,432 | 7/1992 | Haugland et al. | 8/648 |
| 5,269,979 | 12/1993 | Fountain | 424/450 |

OTHER PUBLICATIONS

English language translation of JP 4–29,912, Hino et al., pp. 1–19.

Primary Examiner—Paul Lieberman
Assistant Examiner—Caroline L. Dusheck
Attorney, Agent, or Firm—Flynn, Thiel, Boutell & Tanis, P.C.

[57] ABSTRACT

A hair dye consisting of an anti-hair antibody immobilized on a high bulky coloring material. The coloring material may be a coloring substance such as an inorganic pigment, water-soluble coloring matter, or water-insoluble coloring matter, or a composite of the coloring substance and a macromolecular carrier. Since it provides a good and strong coloring capability specific to hair, the hair dye of the present invention will neither stain the skin nor cause skin irritation. Further, the touch and feel of the hair will be improved.

21 Claims, No Drawings

HAIR COLORING COMPOSITION COMPRISING ANTI-HAIR ANTIBODIES IMMOBILIZED ON COLORING MATERIALS, AND HAIR COLORING METHODS

TECHNICAL FIELD

The present invention relates to hair dyes which are excellent in coloring, are resistant to color fading, do not produce color on skin because of their specific affinity to hair, do not irritate skin and improve the tactile properties of hair.

BACKGROUND ART

For the past years, various methods of dyeing hair have been known in the art. In one of the conventional methods, oxidation dyes are permeated into hair in an alkaline condition, treated with oxidizing agents such as hydrogen peroxide or the like and then are polymerized within the hair for developing color. Alternatively, acid dyes are permeated into the hair for dyeing. There is also another temporary coloring method in which coloring matter or pigment is adhered or fixed to hair using binders for developing colors.

However, those methods are known to have various disadvantages. For example, oxidation dyes pose problems such as damaged hair due to dyeing treatment, allergic effects and irritation to skin, especially to mucus and eye. Although less irritating to skin, the acid dyes are often not satisfactory in finish and disadvantageous in losing color when hair is washed. Skin is sometimes stained by dyes when hair is dyed. The temporary coloring method does not provide a good tactile property because of stickiness, brittleness or the like of applied binders. In addition, resistance to abrasion is generally not sufficient in this method.

Recently, antibodies have been used as cosmetics. For example, Japanese Laid-open Patent Application No. 4-29912 discloses a method in which antibodies are modified with functional molecules of dyes, perfumes, humectants and the like, and then said functional molecules are transferred together with the antibodies to the desired place on account of the specificity of the antibodies.

However, no testing is described about hair dyes in the above patent application though there is a description to the effect that an antibody modified with phycopyrine protein (a fluorescent substance corresponding to a water-soluble natural dye) was applied to skin in an example of the above patent. In addition, according to the above-mentioned method, there exist such problems that sufficient amounts of dyes required to color hair are hardly immobilized on the antibody and that too much load of the dyes may inactivate the antibody. Thus, this method cannot be put into practice.

On the other hand, a method has been known in which antibody-modified pigments are used as diagnostic reagents. However, in this method the pigments are used as a label only for the purpose of the temporary confirmation of the existence of targeted substances, and are not intended to color the targeted substances as dyes. Accordingly, no significant investigations have been conducted on coloring efficiency and color durability (coloring strength) as dyes.

DISCLOSURE OF INVENTION

Therefore it is an object of this invention to provide hair dyes or cosmetics which are excellent in coloring, are resistant to color fading, do not produce color on skin because of their specific affinity to hair, do not irritate skin and improve the tactile properties of hair, and pretreatment agents for strengthening hair dyeing effects and methods for dyeing hair with high effectiveness.

The afore-mentioned object is accomplished by the present invention which comprises:
(1) Hair dyes made of high-bulky coloring materials on which anti-hair antibodies have been immobilized.
(2) Hair dyes for the secondary hair dyeing made of coloring materials on which antibodies having an immunoactivity to anti-hair antibodies have been immobilized.
(3) Pretreatment agents for hair-dye antibodies which contain at least one chemical agent selected from the group consisting of reducing agents, surfactants, alkaline substances and enzymes.
(4) Hair cosmetics or hair care products containing said hair dyes or said secondary hair dyes in an amount of 0.01–80% based on the total weight.
(5) Hair cosmetics or hair care products containing said pretreatment agents for hair-dye antibodies in an amount of 0.01–20% based on the total weight.
(6) A method for dyeing hair in which hair is treated with said pretreatment agents for hair-dye antibodies and then is colored with said hair dyes.
(7) A method for dyeing hair in which hair is treated with the above hair dye and then additionally colored with the above secondary hair dye.

The present invention will be explained in detail hereinafter.

Anti-hair antibodies as used in the present invention are defined as antibodies having an immunoactivity to human hair, and possess a molecular diameter of up to 10 nm. These include antibodies against various components that constitute the hair to be colored. These antibodies can be obtained by immunizing animals using as antigens hair keratin protein, hair cuticle protein, hair matrix protein or fragments thereof. Further, these antibodies can be obtained by using animal nails, body hair, feathers, or extracts and fragments thereof as antigens. In view of differences among species, human hair from either the head or the body is preferably used, and especially various components that constitute human hair are most preferable.

Those animals to be immunized can be selected from domestic animals that include bovines, horses, sheep, goats, rabbits, chickens and the like.

Antibodies can be isolated from milk or colostrum, serum, or egg yolk produced by these animals. The antibodies obtained from bovine milk or colostrum, and egg yolk are preferable because they can be produced in a large quantity.

The raw materials of. the antibody described above can be purified by means of various methods known in the art. For example, after lipid has been removed by suitable methods, crude antigens can be isolated by purification processes including ammonium sulfate fractionation, alcohol precipitation, membrane separation or the like. If required, ion-exchange chromatography and gel-filtration chromatography can be used for further purification. Further, if required, affinity chromatography can be conducted for super purification in which the antigen used in immunization serves as ligand.

The cell fusion process can be conducted between antibody-producing cells and myeloma cells to produce monoclonal antibodies.

The antibodies thus obtained can be digested with enzymes such as papain, pepsin and the like to produce antibody fragments in which the Fc part of immuno-globulin has been severed. Further, the H-chain and L-chain obtained by reducing the antibody with 2-mercaptoethanol may be used.

According to the present invention, antibodies having an immuno-activity to anti-hair antibodies can be obtained by immunizing different species of animals using, as antigens, antibodies and fragments thereof derived from the same animal as the animal immunized in order to obtain said anti-hair antibodies, and possesses about the a same molecular size as that of the anti-hair antibody. Herein these antibodies are referred to as "secondary antibodies". For example, in the case where anti-hair antibodies have been obtained from milk, those antibodies derived from a bovine are used to immunize. animals other than the bovine, for example, rabbits and chickens. In addition, monoclonal antibodies can be used that have an immuno-activity to anti-hair antibodies. These secondary antibodies can be purified in the same manner as described in the case of anti-hair antibodies.

The antibodies thus obtained may be digested with enzymes such as papain, pepsin and the like to produce antibody fragments in which the Fc part of immuno-globulin has been severed. Further, the H-chain and L-chain obtained by reducing the antibody with 2-mercaptoethanol may be used.

In the present invention, said anti-hair antibodies and said secondary antibodies may be collectively referred to as "antibody raw material". The antibody raw materials can be immobilized on coloring materials having at least the same size as them, that is, a substance-constituting unit size of at least about 10 nm. The "substance-constituting unit size" means a "molecular size" in the case of water-soluble coloring substances while it means a "particle size" of materials finely ground in the form of use or fine powder materials in the case of water-insoluble coloring substances.

In this specification, those substances having a maximum substance-constituting unit size in diameter of at least about 10 nm are defined as "high-bulky" while those substances having a substance-constituting unit size less than that diameter are defined as "low-bulky". The substance-constituting unit size of this order can be measured directly by means of electron-microscopic observation, and further can be calculated by applying molecular models in the case of water-soluble coloring substances. Furthermore, "coloring materials" should be understood to refer to coloring substances themselves such as inorganic pigments and organic coloring matter and also to composite substances comprising these coloring substances and macromolecular carriers. Then, "coloring substances" mean low-bulky water-soluble coloring matter, high-bulky water-insoluble coloring matter and inorganic pigments.

In case the coloring materials mean coloring substances themselves, these coloring substances are high-bulky water-insoluble coloring matter and inorganic pigments, and in case the coloring materials are coloring substance/macromolecular carrier composites, the coloring materials can include low-bulky water-soluble coloring matter. In either case, the coloring materials are required to be of high-bulk, that is, of a substance-constituting unit size of at least 10 nm. On the other hand, the coloring materials of low-bulk, that is, of a substance-constituting unit size of less than 10 nm can not provide a sufficient degree of coloring. Nevertheless, the low-bulky coloring materials may be used for immobilizing secondary antibodies. The substance-constituting unit size is desired not to exceed 100 μm. Sizes greater than 100 μm are likely to provide significant negative effects on the tactile properties of dyed hair, and accordingly are considered to be undesirable.

The following table shows the coloring materials of the present invention and the coloring substances that constitute said coloring materials.

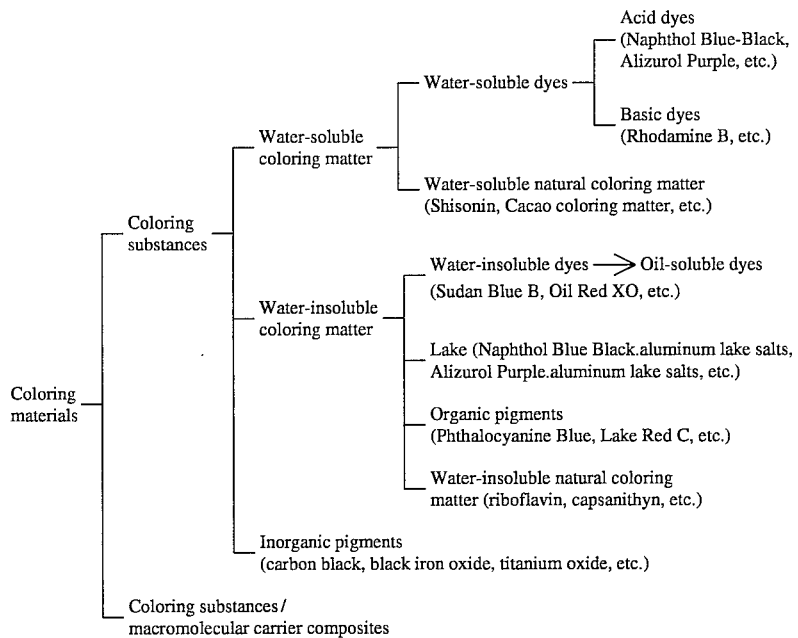

Coloring substances used in the present invention include water-soluble coloring matter such as water-soluble dyes and natural water-soluble coloring matter; water-insoluble coloring matter such as water-insoluble dyes, lakes, organic pigments and water-insoluble natural coloring matter; and inorganic pigments such as titanium oxides such as titan black and titan white; iron oxide and magnetic particles. Among these coloring matters, inorganic pigments and water-insoluble coloring matter are preferred because of lower irritation to skin. Further, the inorganic pigments are preferred because they enable anti-hair antibodies to firmly bind to hair.

In addition, the inorganic pigments are preferably treated with coupling agents or other suitable agents to provide organic functional groups on the surface thereof.

The substance-constituting unit size or particle size of water-insoluble coloring matter and inorganic pigments should be larger than 10 nm to provide coloring substances of high-bulk. The size of the inorganic pigments is preferably in the range of 0.01–6 μm.

Organic pigments applicable to the present invention include Brilliant Fast Scarlet, Permanent Red F5R, Hansa Orange, Hansa Yellow, Phthalocyanine Blue, Lithol Rubine BCA, Lake Red C, Lake Red CBA, Lithol Red, Lithol Red CA, Lithol Red BA, Lithol Red SR, Deep Maroon, Toluidine Red, Permaton Red, Permanent Orange, Benzidine Orange G, Benzidine Yellow G and the like.

High-bulky, water-insoluble dyes applicable to the present invention include Alizarine Cyanine Green F, Quinizarin Green SS, indigo, Carbanthrene Blue, Alizurine Purple SS, medicated Scarlet Blue, Oil Red XO, Orange SS, Yellow AB, Yellow OB, Sudan Blue, Rhodamine B stearate, tetrachloro-tetrabromofluoresceine, tetrabromofluoresceine, Sudan III, dibromofluoresceine, diiodefluoresceine, fluoresceine, Quinoline Yellow SS and the like.

Lakes applicable to the present invention include Naphthol Blue Black·aluminum salt, Alizurol Purple·aluminum Lake salt and the like.

Water-soluble natural coloring matter applicable to the present invention includes shisonin, crocin, Safrole Yellow, Cacao coloring matter, brazilin, and the like.

Water-insoluble natural coloring matters applicable to the present invention include capsanthin, riboflavin, chlorophyll, and the like.

Low-bulky Water-soluble dyes include Pyranine Conc, Light Green SF Yellow, Patent Blue NA, Patent Blue CA, Alphazurin FG, Resorcine Brown, Violamine R, Ponceau 3R, Ponceau R, Ponceau SX, Fast Red S, Orange I, Polar Yellow 5G, Naphthol Yellow S, Metanil Yellow, Fast Light Yellow 3G, Naphthol Green B, Guinea Green B, Alizrol Purple, Naphthol Blue Black, Amaranth, Erythrosine, New Coccine, phloxine B, Rose Bengale, Acid Red, Tartrazine, Sunset Yellow FCF, Fast Green FCF, Brilliant Blue FCF, Indigo Carmine, Lithol Rubine B, Lithol Red, Rhodamine B, Rhodamine B acetate, Fast Acid Magenta, Eosine YS, Eosine YSK, Phloxine BK, Rose Bengale K, Orange II, Erythrocine Yellow NA, uranine, Uranine K, Quinoline Yellow WS and the like.

In the present invention, in the case where said coloring-.materials are high-bulky coloring substances themselves including water-insoluble coloring matter, inorganic pigments and mixtures thereof, anti-hair antibodies can be directly immobilized on said coloring materials, that is, high-bulky coloring substances. The ratio of anti-hair antibodies to coloring substances preferably ranges 1:5–1:100 by weight. Ratios greater than 1:5 are likely to provide insufficient coloring capability. On the other hand, with ratios less than 1:100, no substantial increase in coloring effect is attained, even with an increase in an amount of coloring substances, and especially when the coloring substances are water-soluble coloring matter, the anti-hair antibodies are prone to be deactivated.

Further, said anti-hair antibodies can be immobilized on high-bulky, coloring substances/macromolecular carrier composite coloring materials obtained by combining high-bulky coloring substances including high-bulky water-insoluble coloring matter, inorganic pigments and mixtures thereof with said macromolecular carrier. In these instances, the ratio of said macromolecular carriers to said coloring substances preferably ranges from 1:0.001–1:10 by weight. The secondary antibodies can be immobilized directly on the coloring substances, and the ratio of said secondary antibodies to said coloring substances preferably ranges from 1:0.1–1:100 by weight. In addition, the secondary antibodies can be immobilized on the coloring substances/macromolecular carrier composite coloring materials obtained by combining said coloring substances with said macromolecular carriers, and the ratio of said macromolecular carriers to said coloring substances preferably ranges from 1:0.001–1:10 by weight. Ratios greater than 1:0.001 are likely to provide insufficient coloring capability. On the other hand, with ratios less than 1:10, no substantial increase in coloring effect is attained, even with an increase in an amount of coloring substances.

In the case where said coloring materials are high-bulky coloring substances such as water-insoluble coloring matter and inorganic pigments, either anti-hair antibodies are immobilized directly on them, or said anti-hair antibodies are immobilized on coloring materials made of high-bulky coloring substance/macromolecular carrier composites. Both the above instances would provide a better affinity of an anti-hair antibody to hair as compared with an instance where said anti-hair antibodies are immobilized directly on low-bulky coloring substances such as water-soluble coloring matter. The first instance where said anti-hair antibodies are immobilized directly on the high-bulky inorganic pigments is preferable because of a stronger affinity to hair, and on the other hand the second instance where said anti-hair antibodies are immobilized via the macromolecular carriers on the coloring substances is also preferable because of a significant improvement in functionality. Further, in the case where anti-hair antibodies are immobilized on low-bulky coloring substances made of water-soluble coloring.matter, it is preferable to use coloring substance/macromolecular carrier composites.

The macromolecular carriers used in the present invention are divided into two categories: water-insoluble macromolecular carriers and water-soluble macromolecular carriers. The former water-insoluble macromolecular carriers are advantageous in improvements in tensity, resiliency, tautness, slipperiness, collectivity and feel of hair, and in particular synthetic polymers are preferable because of significant improvement in tensity, resiliency and tautness of hair. In addition to these improvements, water-insoluble proteins can provide suppleness, water-insoluble polysaccharides can provide humid feeling, and liposomes can provide gloss. On the other hand, the latter water-soluble macromolecular carriers are advantageous in improving humid feeling, smoothness, flexibility, slipperiness and feel of hair.

The water-insoluble macromolecular carriers include synthetic polymers, water-insoluble proteins, water-insoluble polysaccharides, liposomes and the like.

The synthetic polymers include polymers such as polystyrene, poly(α-methylstyrene), polyvinyltoluene, polychloromethylstyrene, polychlorostyrene, polyvinylchloride, polyvinylbromide, polyacrylonitrile, polymethacrylonitrile, polyethylacrylate, polyoctylacrylate, polyhydroxypropylacrylate, polybutylacrylate, polymethoxyethylacrylate, polyhydroxyethylacrylate, polylaurylacrylate, polyammoniumacrylate, polymethylmethacrylate, polyethylmethacrylate, polypropylmethacrylate, polybutylaminoethylmethacrylate, polyhydroxymethacrylic acid, polyvinylacetate, polyacrylic acid, polymethacrylic acid, polymaleic acid, polystyrene sulfonic acid, poly(2-acrylamide-2-methylpropane sulfonic acid), polyacrylamide, polymethacrylamide, poly[N-(2-hydroxypropyl) methacrylamide], poly(2-hydroxyethyl methacrylate), poly(glycerol-monomethacrylate), poly(2-oxyethyl acrylate), poly(2-oxyethyl methacrylate), polyethylene glycol methacrylate, polyethylene, polypropylene, polybutene, polyisobutene and the like; copolymers thereof; polyurethanes; copolymers of polyurethane with silicone and the like; nylon beads and the like. Further, those polymers obtained by reforming the surface of the afore-mentioned synthetic polymers also can be used.

Among these synthetic polymers, preferably included are the following groups: hydroxy, halogen, amino, carboxylic, aldehyde, and sulfonic acids. These polymers include polychlorostyrene, polychloromethyl styrene, polyacrylic acid, polymethacrylic acid, polymaleic acid, polystyrene sulfonic acid, poly(2-acrylamide -2-methylpropane sulfonic acid), poly[N-(2-hydroxypropyl) methacrylamide], poly(2-hydroxyethyl methacrylate), poly(glycerol monomethacrylate), poly(2-oxyethyl acrylate), poly(2-oxyethyl methacrylate), polyethylene glycol methacrylate and the like; copolymers thereof; and polymers to which reactivity is provided by surface-reforming. Polystyrene and its derivatives are preferred on account of availability and ease with which particle diameters can be controlled.

As to the water-insoluble proteins, there can be used any proteins that are insoluble in neutral water, and any modified proteins that have been turned water-insoluble by being polymerized by the cross-linkage of water-soluble proteins. They include fibroin, gelatin, collagen and so on.

The water-insoluble polysaccharides include cross-linked agarose, cross-linked dextran, chitin and the like.

As to lipids used as raw materials for liposomes, mention may be made of phospholipids such as phosphatidylcholine, phosphatidylserine, phosphatidyl ethanolamine, and the like.

Particle forms of these water-insoluble macromolecular carriers are not particularly limited in the present invention, and any form such as spheres and plates may be used. Preferably, spheres with a uniform grain size are used. Further, the size is not particularly limited, and preferably is in the range of an average diameter of 0.001–100 μm, and more preferably 0.001–1 μm. The most preferred range is 0.05–0.7 μm with which size a high hair dyeing efficiency can be accomplished.

The ratio of the water-insoluble macromolecular carriers to the antibody raw materials depends on the water-insoluble macromolecular carrier to be used. However, in general 0.01–100 mg of the antibody raw material is preferably immobilized on 1 g of the water-insoluble macromolecular carrier. Less than 0.01 mg is likely to provide insufficient coloring capability. On the other hand, with the addition of more than 100 mg, no substantial increase in coloring capability is attained.

As to the water-soluble macromolecular carriers, either natural or synthetic ones can be used, which include polysaccharides and proteins of natural origin and derivatives thereof.

Those polysaccharides include starch, amylose, amylopectin, pectin, carrageenan, mannan, galactan, sodium alginate, tragacanth gum, gum arabic and the like, of vegetable origin; dextran, pullulan, Curdlan, levan, glucan, succinoglucan, Xanthane Rubber and the like, of microorganisum origin; and hyaluronic acid, chondroitin sulfate and the like, of animal origin.

Those proteins include glue, gelatin, casein, collagen, fibroin and the like.

The semi-synthetic polymers include viscose, methyl cellulose, ethyl cellulose, hydroxyethyl cellulose, hydroxypropyl cellulose, carboxymethyl cellulose, solubilized starch, carboxymethyl starch, dialdehyde starch and the like.

The synthetic polymers include polyvinylalcohol, carboxyvinyl polymers, polysodiumacrylate, polyvinylpyrrolidone, polyethyleneoxide, polylysine, polyglutamic acid, polyaspartic acid and the like.

Any molecular form of these water-soluble macromolecular carriers, either of straight chain or branched chain can be used. Preferably, polymers with a uniform molecular weight distribution are used, and preferably is in the range of an number-averaged molecular weight of 10,000–2,000,000. In addition, the average substance-constituting unit size or molecular size is preferred to be in the range of 0.01–5 μm.

The ratio of the water-soluble macromolecules to the antibody raw materials depends on the water-soluble macromolecule to be used. However, in general, 0.01 mg–1 g of the antibody raw material is preferably immobilized on 1 g of the water-soluble macromolecule.

Hair dyes of the present invention can be produced using the antibody raw materials according to the following methods, but methods of the invention are not limited to those methods described herein.

According to the present invention, in order to immobilize coloring substances such as water-insoluble coloring matter and inorganic pigments directly on the antibody raw materials, physical adsorption and chemical binding are utilized.

Physical adsorption can occur while the water-insoluble coloring matter and inorganic pigments are mixed with the antibody raw materials.

Chemical binding can occur when the waterinsoluble coloring matter or inorganic pigments possess organic functional groups. In the case of inorganic pigments that usually lack organic functional groups, it is necessary to introduce organic functional groups on the surface of the pigment. Treatments using coupling agents and silicone treatment can be used for the introduction of organic functional groups on the surface of the pigment. The coupling agents include silane coupling agents, titanate coupling agents, aluminate coupling agents, zirco-aluminate coupling agents and the like. Amino-modified silicone and carboxyl-modified silicone and the like are used for the silicone treatment.

For example, 3-aminopropyl triethoxy silane can be reacted to introduce amino groups to the pigment surface. Reaction of the amino group with glutaric anhydride or succinic anhydride can transform the amino group to a carboxyl group. Further, 3-mercaptopropyl triethoxy silane can react to introduce an SH group to the pigment surface.

These organic functional groups can be combined with the antibody raw materials according to any well-known methods. If the organic functional group is an amino group, then glutaraldehyde is used to combine it while a carboxyl group can be combined with 1-ethyl-3-(3-dimethylaminopropyl)carbodiimide (abbreviated as EDC hereinafter). If an SH group is combined, cross-linking reagents as exemplified by N-succinimidyl-3-(2-pyridyl dithio)propionate (abbreviated as SPDP hereinafter) can be used.

According to the present invention, in order to support coloring substances such as water-soluble coloring matter, water-insoluble coloring matter, inorganic pigments and the like on the water-insoluble macromolecular carriers or water-soluble macromolecular carriers, physical and chemical methods are utilized.

The physical methods include an adsorption method in which the coloring substances are adsorbed on the water-insoluble macromolecular carriers, an internal addition method in which the coloring substances are added to the water-insoluble macromolecular carrier during its manufacture, an inclusion method in which the coloring substances are included within the water-insoluble macromolecular carriers, and a polymerization method in which coloring matter precursors are polymerized within the water-insoluble macromolecular carriers.

The chemical binding also can immobilize the coloring substances if functional groups exist in the water-insoluble or water-soluble macromolecular carriers. The functional groups include amino groups, carboxyl groups, aldehyde groups, hydroxyl groups, thiol groups, and the like. Polysaccharides can be used per se, but may be chemically modified, if required. For example, polysaccharides can be oxidized with metaperiodate acid and the like to form aldehyde groups. Diamines can be reacted with the aldehyde groups to introduce an amino group while ε-aminocaproic acid can be reacted with the aldehyde groups to introduce a carboxyl group. In addition, activation reagents such as cyanuric chloride and cyanogen bromide can be reacted with polysaccharides to form activated polysaccharides.

According to the present invention, in order to immobilize antibodies on water-insoluble or water-soluble macromolecular carriers, physical adsorption and chemical binding are utilized.

The functional groups of antibody raw materials that are used for the chemical binding include amino groups, carboxyl groups, aldehyde groups, thiol groups, polysaccharide chains and the like, which can be immobilized in the same manner as in the binding between coloring substances and carriers. For example, when polysaccharide are used for binding, the saccharide chain portions can be oxidized with metaperiodate and the like to form aldehyde groups, which are then reacted with amino groups of the carriers to form Schiff bases, thus resulting in immobilization. Thiols can be reacted with SPDP reagents for immobilization.

In manufacturing the aforementioned antibody raw materials immobilized coloring materials, ratios of the antibody raw materials to coloring materials and ratios of the macromolecular carriers to the coloring substances can be changed so that their ratios in the antibody-immobilized coloring materials thus formed can be adjusted to obtain desired ratios of their components.

Hair dyes comprising the antibody raw materials-immobilized coloring materials that have been obtained as described above can be put into practice as solutions in appropriate solvents, such as aqueous solution, or as dispersions, or as dried products that are obtained by means of freeze-drying or spray-drying.

The hair dyes of the present invention possess sufficient amounts of coloring substances to be required for coloring so that they specifically react and combine with hair to effect coloring. Further, in the case of hair dyes using macromolecular carriers, there are achieved extraordinary improvements in functions of hair. In the case where the macromolecular carriers are water-insoluble macromolecular carriers, there will be improvements in tensity, resiliency, tautness, slipperiness, collectivity and tactile properties of the hair. In addition to these improvements, water-insoluble proteins can provide suppleness, water-insoluble polysaccharides can provide humid feel, and liposomes can provide gloss. On the other hand, the water-soluble macromolecular carriers are advantageous in improvement in humid feel, smoothness, suppleness, slipperiness and tactile properties of the hair. Hair dyes in which antibody raw materials have been immobilized directly to water-soluble macromolecular carriers or inorganic pigments according to the present invention will have a stronger bonding to hair as compared with conventional coloring matter-direct bonded antibodies.

The antibody raw materials-immobilized coloring materials of the present invention can be incorporated into conventional hair cosmetics in suitable amounts to provide useful hair cosmetics. Hair cosmetics that contain only conventional hair dyes, when applied to hair, may color the very scalp in a certain case, or in another case, do not have sufficient concentrations due to fear of skin troubles, resulting in poor coloring capability. Thus, it has been quite troublesome to repeat hair dyeing operations until a desired degree of coloring is reached since only a small degree of coloring is attained with a single hair dyeing operation. However, the hair cosmetics of the present invention can provide satisfactory hair dyeing effects with only a single action of dyeing while causing no staining on the scalp at all, since the hair dye contains a sufficient amount of anti-hair antibody immobilized coloring materials which bond specifically to hair.

The hair cosmetics of the present invention can be prepared by compounding said hair dyes together with a conventional substrate for hair cosmetics. Forms suitable for such hair cosmetics include shampoo, rinse, styling foam, hair conditioner, hair pack, hair cream, hair liquid, hair tonic, permanent wave reagents, hair manicures and the like.

The content of hair dye in the hair cosmetics of the present invention may be determined suitably based on the types of cosmetics, types of coloring substances, types and sizes of carriers and the like. In general, based on the total weight of the cosmetics, its content ranges 0.01–80% by weight with the balance being conventional substrates for hair cosmetics.

Reducing agents used for pretreating the hair dye antibody of the present invention include sodium hydrogen sulfite, sodium sulfite, potassium pyrosulfate, sodium pyrosulfate, sodium thiosulfate, L-cysteine, thioglycolic acid, 2-mercaptoethanol, 2-mercaptopropionic acid, thioglycerol and the like. Surfactants include SDS (sodium dodecyl sulfonate) and the like. Alkaline substances include ammonia, monoethanolamine and the like. Enzymes include papain, trypsin and the like.

Pretreatment of hair is conducted by treating hair with an aqueous solution containing said pretreatment agents. Further, in this pretreatment step, ultrasonic application can increase pretreatment efficiency.

The obtained pretreatment agents for hair dye antibodies can be compounded together with conventional substrates for hair cosmetics to produce the hair cosmetics of this invention.

The content of the pretreatment agent for hair dye antibodies in the hair cosmetics of the present invention can be determined suitably based on the types of cosmetics and types of pretreatment agents and the like. In general, based on the total weight of the cosmetics, its content ranges 0.01–20% by weight with the balance being conventional substrates for hair cosmetics.

In order to color hair with the hair dyes of this invention or with the hair cosmetics containing said hair dyes, it is sufficient only to apply the hair dyes made of anti-hair antibodies or the hair cosmetics containing said hair dyes. In addition, if hair is treated in advance with the pretreatment agents of this invention for hair dye antibodies or with the hair cosmetics containing said pretreatment agents, then hair coloring efficiency will be increased greatly, and this pretreatment is preferable. Furthermore, if hair is colored additionally with the secondary hair dyes made of secondary antibodies or antibodies having an immuno-activity to anti-hair antibodies or with the cosmetics containing said secondary hair dyes, then hair coloring efficiency also will be increased greatly. Further, hues of hair after having been dyed can be changed by using coloring substances of types different from the type used the previous time.

THE BEST MODES FOR CARRYING OUT THE INVENTION

The present invention will be explained using the following examples, but are not limited to these examples. Percentages as described in the examples are based on weight unless specifically noted.

Example 1 Anti-Keratin Antibody-Immobilized Titan Black Hair Dyes (1) Preparation of Antigens 5 g of male healthy hair and 5 g of female healthy hair were mixed, and washed with a 2% sodium polyoxyethylene laurylether sulfate (3 E.O.) aqueous solution. The washed healthy hair was agitated under $N_2$ bubbling in a 2.5 l 0.2M Tris-HCl buffer solution (pH 9.2) containing 8M urea and 0.2M 2-mercaptoethanol at 50° C. for one hour, and then ground with a TEFLON® homogenizer. The above extraction procedure was repeated and the obtained extract was subjected to 1,000 × g centrifugation for 30 minutes to remove impurities and to obtain a hair keratin antigen extract. 200 g of monoiodide acetic acid (which was dissolved in 760 ml solution containing 400 g tris) was then added to the extract for the reaction conducted while stirring in darkness at room temperature for one hour. 7 ml of 2-mercaptoethanol was added to stop the reaction. The resulting mixture was sufficiently dialyzed against distilled water. A 5 μm filter was used to remove insolubles to obtain 6 l of an aqueous solution of hair keratin antigen. To 4 parts by volume of this solution was added 1 part by volume of a 0.25M sodium acetate buffer solution (adjusted to pH 4.2 with acetic acid), and hair keratin was precipitated at the isoelectric point. The precipitate thus obtained was then centrifuged with a 10,000× g force for 10 minutes. The supernatant was removed to collect the precipitate which was then dissolved in physiological salt water. A 0.2 μm filter was used to remove germs from the solution which was then concentrated using ultrafiltration membranes to obtain purified hair keratin antigen (2.6 g as protein).

(2) Preparation of Anti-Keratin Antibody (Immunization Into Cow)

The protein concentration of said purified hair keratin antigen solution was adjusted at 20 mg/ml with physiological salt water. The solution and complete Freund's adjuvant were mixed at a volume ratio of 1:1 to prepare a water-in-oil emulsion. Two heads of pregnant Holstein cows 2 months before parturition were injected with 5.0 ml each of said emulsion subcutaneously in the neck. Subsequently, with an interval of 10 days an, emulsion that had been prepared with incomplete Freund's adjuvant and that contained the same amount of antigen as in the first-time immunization was injected subcutaneously or intramuscularly for immunization. (1st–3rd immunization: hypodermic injection, 4–5th immunization: intramuscular injection).

(Collection and purification of antibody)

Colostrum was collected from the cows immunized as described above for three days immediately after parturition. A cream separator was used to separate the fat layer of the colostrum to obtain skimmed milk. From the skimmed milk thus obtained, fractional purification of antibodies was conducted by the following procedure.

To the skimmed milk was added 0.1N HCl to adjust the pH at 4.5 to precipitate casein. The precipitate was roughly filtered out. The supernatant was obtained through a continuous centrifugation at 2,500× g. The obtained supernatant was neutralized. Ammonium sulfate was added to obtain a 33% saturated liquid from which the antibody was salted out. Precipitates were collected by a 2,500× g centrifugation, and dissolved in a phosphate buffered saline solution (abbreviated as PBS hereinafter). This ammonium sulfate salt-out procedure was repeated. The resulting solution was dialyzed against a 10 mM PBS (pH 7.5). The solution was divided into 5 aliquots, each of which was applied to a 2 l DEAE cellulose column (DE-52, made by Whatman) that had been equilibrated with said buffer solution. Unadsorbed proteins were washed away by said buffer solution. Afterwards, the antibody was eluted with said buffer solution containing 50 mM NaCl, and the antibody fractions (200 g as antibody) were collected. The fractions had an antibody purity of 90% or higher. The fraction was divided into 5 aliquots, each of which was provided to 400 ml affinity resin (Affi-Gel 15, Bio-Rad, Inc.) to which purified hair keratin had been conventionally bound. Anti-hair keratin antibodies adsorbed to the affinity resin were eluted with a 0.2M glycine HCl buffer solution (pH 2.5), and immediately pH adjusted to around 8 with a 3M tris solution. Then, the anti-hair keratin antibody (affinity-purified) that specifically binds to the hair keratin antigen was obtained. For simplicity, this antibody will be referred to as an anti-keratin antibody hereinafter.

(3) Preparation of Control Antibody

Antibodies were obtained from the colostrum of nonimmunized cows and were purified by means of the same methods as described above to obtain control antibodies. The control antibodies used in the comparative examples had been purified in a DEAE-cellulose column and had an antibody purity of 90% or more.

(4) Immobilization of Anti-Keratin Antibody on Titan Black (Surface Modification of Titan Black)

1 g of Titan Black 10 S (average particle diameter of 0.025 μm, produced by Mitsubishi Metal Co.) was dispersed in 10 ml of distilled water using ultrasonic waves. To this dispersion liquid was added 75 μl of an aqueous 1% 3-aminopropyl triethoxysilane solution, and the resulting mixture was agitated at room temperature for 2 hours. While being heated at 40° C., the mixture was dewatered under a vacuum in an evaporator Then, 10 minutes' drying operation at 110° C. introduced amino groups on the surface of the Titan Black.

(Reaction between Silane-treated Titan Black and Glutaric aldehyde)

80 mg of Titan Black to which an amino group had been introduced by silane treatment was dispersed in 4 ml of distilled water using ultrasonic waves. To this dispersion liquid was added 4 ml of an aqueous 0.25% glutaric aldehyde solution, and the resulting mixture was agitated at room temperature for 2 hours. Then, the mixture was centrifuged at 20° C., 10,000 rpm for 20 minutes, and then redispersed in 8 ml of distilled water. This washing procedure was repeated 5 times.

(Reaction of Titan Black with Anti-Keratin Antibody)

To 0.5 ml of a 1% Titan Black dispersion liquid treated with glutaric aldehyde was added 0.5 ml of an anti-keratin antibody solution that had been adjusted to 10 mg/ml with PBS, and the resulting mixture was agitated at 4° C. overnight. Then, the mixture was centrifuged at 20° C., 12,000 rpm for 20 minutes, and then redispersed in 0.5 ml of PBS containing 0.1% bovine serum albumin (abbreviated as BSA hereinafter). Further, the mixture was centrifuged at 20° C., 12,000 rpm for 20 minutes, and then redispersed in 0.5 ml of PBS containing 0.1% BSA, and afterwards incubated at room temperature for 1 hour. Then, to this mixture was added 10 μl of an aqueous 0.005M sodium borohydride solution, and the resultant mixture was incubated at room temperature for 1 hour, and then centrifuged at 20° C., 12,000 rpm for 20 minutes. The mixture was then redispersed into 0.5 ml of PBS containing 0.1% TWEEN 20 (polyoxyethylene sorbitan monolaurate, 20 E.O.) and 0.1% BSA. On the hair dye thus obtained, it was found, 144 mg of the antibody per 1 g of the Titan Black had been immobilized.

Comparative Example 1

Instead of the anti-keratin antibody produced in Example 1, the control antibody produced in Example 1(3) was immobilized on Titan Black. This Titan Black was used to produce a hair dye which was designated as Comparative Example 1. On the hair dye thus obtained, it was found, 243 mg of the antibody per 1 g of the Titan Black had been immobilized.

Example 2 Anti-Keratin Antibody-Immobilized Titan Black Hair Dye (Reaction between Silane-treated Titan Black and Glutaric Anhydride)

25 mg of Titan Black that had been treated with silane in Example 1(4) was dispersed in 4 ml of an aqueous 0.1M sodium hydrogen carbonate. Then, the mixture was centrifuged at 20° C., 10,000 rpm for 20 minutes, and then redispersed in 4 ml of an aqueous 0.1M sodium hydrogen carbonate. This procedure was repeated 4 times. At the last step, the mixture was redispersed in 0.5 ml of an aqueous 0.1M sodium hydrogen carbonate. To this mixture was added 50 μl of glutaric anhydride aqueous solution (57 mg/ml), and the resulting mixture was agitated at room temperature for 1 hour to effect reaction. Then, the mixture was centrifuged at 20° C., 10,000 rpm for 20 minutes, and then redispersed in 4 ml of an aqueous 0.1M sodium hydrogen-carbonate. This procedure was repeated 3 times. At the last step, the mixture was redispersed in 0.5 ml of an aqueous 0.1M sodium hydrogen carbonate.

To this mixture was added 50 μl of glutaric acid anhydride aqueous solution (57 mg/ml), and the resulting mixture was agitated for reaction at room temperature for 1 hour. Then, the mixture was centrifuged at 20° C., 10,000 rpm for 20 minutes, and afterwards the reactant was removed. The, the mixture was redispersed in 4 ml of an aqueous 0.1M sodium hydrogen carbonate, and centrifuged at 20° C., 10 000 rpm for 20 minutes for washing the Titan Black. This operation was repeated 2 times. At the last step, the mixture was redispersed in 0.5 ml of an aqueous 0.1M sodium hydrogen carbonate. Again, to this mixture was added 50 μl of gluralic anhydride aqueous solution (57 mg/ml), and the resulting mixture was agitated for reaction at room temperature for 1 hour. Then, the mixture was centrifuged at 20° C., 10,000 rpm for 20 minutes, and afterwards the reactant was removed. The, the mixture was redispersed in 4 ml of distilled water, and centrifuged at 20° C, 10,000 rpm for 20 minutes for washing the Titan Black. This operation was repeated 4 times. At the last step, the mixture was redispersed in 2.5 ml of distilled water. These treatments provided Titan Black to which a carboxyl group had been introduced.

(Reaction of Titan Black with Anti-Keratin Antibody)

The pH of a 1% Titan Black aqueous dispersion liquid to which a carboxyl group had been introduced with gluralic anhydride treatment was adjusted to be 5. To 0.5 ml of this dispersion liquid was added 0.5 ml of a 0.002M EDC aqueous solution, and the resulting mixture was agitated for reaction at room temperature for 2 hours. Then, the mixture was centrifuged at 20° C., 12,000 rpm for 20 minutes, and then redispersed in 0.5 ml of distilled water. To this EDC-activated Titan Black was added 0.5 ml of the anti-keratin antibody solution that had been adjusted to 10 mg/ml with PBS as in Example 1(2), and then the mixture was agitated at 4° C. overnight. Afterwards, the resultant mixture was centrifuged at 20° C., 12,000 rpm for 20 minutes, and then redispersed into 0.5 ml of PBS containing 0.1% BSA. Again, this was centrifuged at 20° C., 12,000 rpm for 20 minutes, and then redispersed in 0.5 ml of PBS containing 0.1% BSA., and afterwards incubated at room temperature for 1 hour. Then, this was centrifuged at 20° C., 12,000 rpm for 20 minutes, and then redispersed in 0.5 ml of PBS containing 0.1% TWEEN 20 and 0.1% BSA. On the hair dye thus obtained, it was found, 166 mg of the antibody per 1 g of the Titan Black had been immobilized.

Comparative Example 2

Instead of the anti-keratin antibody produced in Example 2, the control antibody produced in Example 1(3) was immobilized on Titan Black. This Titan Black was used to produce a hair dye which was designated as Comparative Example 2.

Example 3 Anti-Keratin Antibody-Immobilized Titan Black Hair Dye (Surface Modification of Titan Black)

1 g of Titan Black 10S (produced by Mitsubishi Metal Co.) was dispersed in 20 ml of distilled water using ultrasonic waves. To this dispersion liquid was added 15 μl of a zircoaluminate coupling agent having carboxyl groups (type C, produced by MANCHEM, Inc.), and the resulting mixture was agitated at room temperature for 2 hours. While being heated at 40° C., the mixture was dewatered under a reduced pressure in an evaporator. Then, 10 minutes of a drying operation at 110° C. produced a Titan Black treated with the zircoaluminate coupling agent. This treatment could provide a Titan Black on the surface of which a carboxyl group had been introduced.

(Reaction of Titan Black with Antibody)

The Titan Black on the surface of which a carboxyl group has been introduced by means of the zircoaluminate coupling treatment was dispersed into distilled water at a concentration of 1%. To 0.5 ml of this dispersion liquid was added 0.5 ml of a 0.002M EDC aqueous solution, and the resulting mixture was agitated for reaction at room temperature for 2 hours. Then, the mixture was centrifuged at 20° C., 12,000 rpm for 20 minutes, and then redispersed in 0.5 ml of distilled water. To this EDC-activated Titan Black was added 0.5 ml of the anti-keratin antibody that had been adjusted to 10 mg/ml with PBS as in Example 1(2), and then the mixture was agitated at 4° C. overnight. Afterwards, the resultant mixture was centrifuged at 20° C., 12,000 rpm for 20 minutes, and then redispersed in 0.5 ml of PBS containing 0.1% BSA. Again, this was centrifuged at 20° C., 12 000 rpm for 20 minutes, and then redispersed in 0.5 ml of PBS containing 0.1% BSA., and afterwards incubated at room temperature for 1 hour. Then, this was centrifuged at 20° C., 12,000 rpm for 20 minutes, and then redispersed in 0.5 ml of PBS containing 0.1% TWEEN 20 and 0.1% BSA. On the hair dye thus obtained, it was found, 60 mg of the antibody per 1 g of the Titan Black had been immobilized.

Comparative Example 3

Instead of the anti-keratin antibody produced in Example 3, the control antibody produced in Example 1(3) was immobilized on Titan Black. This Titan Black was used to produce a hair dye which was designated as Comparative Example 3.

Example 4 Anti-Keratin Antibody-Immobilized Carbon Black Hair Dye (Reaction of Carbon Black with Antibody)

60 g of Carbon Black MA 100 (an average particle diameter of 0.022 μm, produced by Mitsubishi Chemicals Co.) was dispersed in 10 ml of a 0.05 % TWEEN 20 solution using ultrasonic waves. To 10 ml of this carbon black dispersion liquid was added 10 ml of a 0.02M EDC aqueous solution, and the resulting mixture was agitated for reaction at room temperature for 2 hours. Then, the mixture was centrifuged at 20° C., 10 000 rpm for 20 minutes to remove unreacted EDC. The EDC-activated carbon black was redispersed in 10 ml of the 0.05 % TWEEN 20 solution. That is, 0.5 ml of a 0.6 %arbon black dispersion liquid was charged into a tube to which also 0.5 ml of the anti-keratin antibody that had been adjusted to a protein concentration of 1.0 mg/ml with PBS as in Example 1(2) was added, and then the mixture was agitated at 4° C. overnight. After completion of the reaction, the resultant mixture was centrifuged at 20° C., 10,000 rpm for 20 minutes, and then the carbon black thus obtained was redispersed in 1.0 ml of PBS containing 0.1% BSA. Further, this was centrifuged at 20° C,, 10,000 rpm for 20 minutes, and then redispersed in 1.0 ml of PBS containing 0.1% BSA., and afterwards incubated at room temperature for 1 hour. Then, this was centrifuged at 20° C., 10,000 rpm for 20 minutes, and then redispersed in 1.0 ml of PBS containing 0.1% TWEEN 20 and 0.1% BSA. Finally, a 0.6% carbon black dispersion liquid to which an anti-keratin antibody had bound was obtained.

Comparative Example 4

Instead of the anti-keratin antibody produced in Example 4, the control antibody produced in Example 1(3) was immobilized on carbon black. This carbon black was used to produce a hair dye which was designated as Comparative Example 4.

Example 5 Anti-Keratin Antibody-Immobilized Carbon Black Hair Dye (Surface Modification of Carbon Black)

To 2.5 g of Carbon Black No. 4 (an average particle diameter of 0.025 μm, produced by Degussa Co.) was added 50 ml of distilled water or isopropyl alcohol, and the mixture was dispersed using ultrasonic waves. To this dispersion liquid was added 16.5 μl of a zircoaluminate coupling agent (type C, produced by MANCHEM, Inc.), and the resulting mixture was agitated at room temperature for more than 2 hours. While being heated at 40° C. or higher, the mixture was dehydrdated under a reduced pressure in an evaporator. Then, the product was dried at 110° C. for 15 minutes. This process could provide a carbon black on the surface of which a carboxyl group had been introduced.

(Reaction of Carbon Black with Antibody)

Carbon Black No. 4 to which a carboxyl group had been introduced was dispersed in distilled water so that its concentration was 1%. To 0.5 ml of this carbon black dispersion liquid was added 0.5 ml of a 0.02M EDC aqueous solution, and the resulting mixture was agitated for reaction at room temperature for 2 hours. Then, the mixture was centrifuged at 20° C., 14,500 rpm for 20 minutes to remove unreacted EDC. The EDC-activated carbon black was redispersed in 0.5 ml of distilled water for use of combination with an antibody. That is, 0.5 ml of a 1.0% carbon black dispersion liquid was charged into a tube to which also 0.5 ml of the anti-keratin antibody that had been adjusted to a protein concentration of 10 mg/ml with PBS as in Example 1(2) was added, and then the mixture was agitated for reaction at 4° C. overnight. After completion of the reaction, the resultant mixture was centrifuged at 20° C., 14,500 rpm for 20 minutes, and then the carbon black thus obtained was redispersed in 1.0 ml of PBS containing 0.1% BSA. Further, this was centrifuged at 20° C., 14,500 rpm for 20 minutes, and then redispersed in 0.5 ml of PBS containing 0.1% BSA, and afterwards incubated at room temperature for 1 hour. Then, this was centrifuged at 20° C., 14,500 rpm for 20 minutes, and then redispersed in 0.5 ml of PBS containing 0.1% TWEEN 20 and 0.1% BSA. Finally, a 1.0% carbon black dispersion liquid to which an anti-keratin antibody had bound was obtained.

Comparative Example 5

Instead of the anti-keratin antibody produced in Example 5, the control antibody produced in Example 1(3) was immobilized on carbon black. This carbon black was used to produce a hair dye which was designated as Comparative Example 5.

Example 6 Anti-Keratin Antibody-Immobilized Iron Oxide Hair Dye (Surface Modification of Iron Oxide)

Water-insoluble polyacrylic acid polymer was dissolved in toluene to prepare a 5% polyacrylic acid polymer solution. To this solution was added 25% by weight of iron oxide (an average particle diameter of 0.02×0.06 μm), and the mixture was dispersed well using ultrasonic waves. After complete dispersion, the mixture was then heated for evaporation of toluene to obtain the iron oxide coated with polyacrylic acid polymers.

(Reaction of Iron Oxide with Antibody)

The polymer coated iron oxide was dispersed in distilled water at a solids concentration of 1%. Afterwards, HCl was used to adjust the pH to 5. To 1 ml of this dispersion liquid was added 1.0 ml of a 0.01M EDC aqueous solution, and the resulting mixture was agitated for reaction at room temperature for 2 hours. Then, the mixture was centrifuged to remove supernatant, and redispersion operations were conducted with additional uses of 1.0 ml of PBS. To this was added 1.0 ml of the anti-keratin antibody that had been adjusted to a concentration of 1.0 mg/ml with PBS as in Example 1(2), and then the mixture was agitated at 4° C. overnight. After centrifugation, the supernatant was removed, and redispersion operations were conducted with additional uses of 1.0 ml of PBS containing 0.1% BSA. Afterwards, the mixture was incubated at room temperature for 1 hour to conduct blocking by BSA. Further, after centrifugation, redispersion was conducted with the addition of 1.0 ml of PBS containing 0.1% TWEEN 20 and 0.1% BSA. Finally, iron oxides to which anti-keratin antibodies had been chemically bound were obtained.

Comparative Example 6

Instead of the anti-keratin antibody produced in Example 6, the control antibody produced in Example 1(3) was immobilized on iron oxides. The iron oxides were used to produce a hair dye which was designated as Comparative Example 6.

Example 7 Anti-Keratin Antibody-Immobilized Colored Latex Hair Dye

Water-insoluble carboxy-modified-polystyrene latex (an average particle diameter of 0.19 μm, produced by Japan Synthetic Rubber Co.) on which a red coloring matter had been adsorbed was dispersed in distilled water at a solids concentration of 1%. Afterwards, HCl was used to adjust the pH to 5. To 1 ml of this latex aqueous dispersion was added 1.0 ml of a 0.01M EDC aqueous solution, and the resulting mixture was agitated at room temperature for 2 hours. Then, the mixture was centrifuged to remove supernatant, and redispersion operations were conducted with additional uses of 1.0 ml of PBS. To this was added 1.0 ml of the anti-keratin antibody that had been adjusted to a concentration of 1.0 mg/ml with PBS as in Example 1(2), and then the mixture was agitated at 4° C. overnight. After centrifugation, the supernatant was removed, and redispersion operations were conducted with additional uses of 1.0 ml of PBS containing 0.1% BSA. Afterwards, the mixture was incubated at room temperature for 1 hour to conduct unreacted site blocking by BSA. Further, after centrifugation, redispersion was conducted with the addition of 1.0 ml of PBS containing 0.1% TWEEN 20 and 0.1% BSA. Finally, a colored latex to which anti-keratin antibodies had been chemically bound were obtained. On the hair dye thus obtained, it was found, 50–80 mg of the antibody per 1 g of the colored latex had been immobilized.

Comparative Example 7

Instead of the anti-keratin antibody produced in Example 7, the control antibody produced in Example 1(3) was combined with the colored, water-insoluble latex. The latex thus obtained was used to produce a hair dye which was designated as Comparative Example 7. On the hair dye thus obtained, it was found, that 50–80 mg of the antibody per 1 g of the colored latex had been immobilized.

Example 8 Anti-Keratin Antibody-Immobilized Colored Latex Hair Dye

Water-insoluble carboxy-modified-polystyrene latex (an average particle diameter of 0.19 μm) on which red coloring matter had been adsorbed was dispersed in distilled water at a solids concentration of 1%. To 1 ml of this dispersion was added 1.0 ml of the anti-keratin antibody that had been adjusted to a concentration of 1.0 mg/ml with PBS as in Example 1(2), and then the mixture was agitated at 4° C. overnight. After centrifugation, the supernatant was removed, and a redispersion procedures was conducted with additional uses of 1.0 ml of PBS containing 0.1% BSA. Further, procedures of centrifugation and redispersion were repeated, and then redispersion was conducted with the addition of 1.0 ml of PBS containing 0.1% TWEEN 20 and 0.1% BSA. Finally, a colored latex on which anti-keratin antibodies had been immobilized by means of physical adsorption was obtained. On the hair dye thus obtained, it was found, 50–80 mg of the antibody per 1 g of the colored latex had been immobilized.

Comparative Example 8

Instead of the anti-keratin antibody produced in Example 8, the control antibody produced in Example 1(3) was adsorbed to the colored, water-insoluble latex. The latex thus obtained was used to produce a hair dye which was designated as Comparative Example 8. On the hair dye thus obtained, it was found that 50–80 mg of the antibody per 1 g of the color latex had been immobilized.

Example 9 Anti-Keratin Antibody-Immobilized Colored Latex Hair Dye

Water-insoluble carboxy-modified-polystyrene latex (an average particle diameter of 0.15 μm) on which Carbon Black MA 100 as a black pigment had been included was dispersed in distilled water at a solids concentration of 1%. Afterwards, the pH was adjusted to 5 by HCl. To 1 ml of this latex aqueous dispersion was added 1.0 ml of a 0.01M EDC aqueous solution and the resultant mixture was agitated at room temperature for 2 hours. After centrifugation, the supernatant was removed, and redispersion operations were conducted with additional uses of 1.0 ml of PBS. This was admixed with 1 ml of the anti-keratin antibody that had been adjusted to a concentration of 1.0 mg/ml with PBS as in Example 1(2), and then was agitated at 4° C. overnight. After centrifugation, the supernatant was removed, and redispersion operations were conducted with additional uses of 1.0 ml of PBS containing 0.1% BSA. Then, the solution was incubated at room temperature for 1 hour followed by blocking of unreacted sites with BSA. Further, after centrifugation, redispersion was conducted with the addition of 1.0 ml of PBS containing 0.1% TWEEN 20 and 0.1% BSA. Finally, a colored latex to which anti-keratin antibodies had been bound by means of a chemical bond was obtained.

Comparative Example 9

Instead of the anti-keratin antibody produced in Example 9, the control antibody produced in Example 1(3) was combined with the colored, water-insoluble latex. The latex thus obtained was used to produce a hair dye which was designated as Comparative Example 9.

Example 10 Anti-Keratin Antibody-Immobilized Colored Latex Hair Dye

Water-insoluble carboxy-modified-polystyrene latex (an average particle diameter of 0.15 μm) on which Carbon Black MA 100 as a black pigment had been included was dispersed in distilled water at a solid concentration of 1%. 1 ml of this dispersion liquid was admixed with 1 ml of the anti-keratin antibody that had been adjusted to a protein concentration of 1 mg/ml with PBS as in Example 1(2), and then the mixture was agitated at 4° C. overnight. After centrifugation, the supernatant was removed, and redispersion operations were conducted with additional uses of 1.0 ml of PBS containing 0.1% BSA. Further, after operations of centrifugation and redispersion were repeated, redispersion was conducted with the addition of 1.0 ml of PBS containing 0.1% TWEEN 20 and 0.1% BSA. Finally, a colored latex on which anti-keratin antibodies had been immobilized by means of physical adsorption was obtained.

Comparative Example 10

Instead of the anti-keratin antibody produced in Example 10, the control antibody produced in Example 1(3) was adsorbed on the colored, water-insoluble latex. The latex thus obtained was used to produce a hair dye which was designated as Comparative Example 10.

Comparative Example 11

A hair dye was prepared by combining the antibodies as prepared in Example 1(2) directly with red coloring matter (water-soluble coloring matter) in an equimolar amount without water-insoluble macromolecular carriers.

Comparative Example 12

A hair dye was prepared by combining the antibodies as prepared in Example 1(2) directly with red coloring matter (water-soluble coloring matter) in an excessive molar amount without water-insoluble macromolecular carriers.

Test Example 1 Agglutination Test

The hair-keratin antigens produced in Example 1(1) were adjusted with PBS at a 100 µg concentration. The hair-keratin solution was mixed with those hair dyes of Examples 1–10 and Comparative Examples 1–12 on an equal amount basis, and whether or not agglutination occurred after 1 minute was judged. The results are shown in Table 1. In this table, the sign "−" denotes that no agglutination was observed while the sign "+" denotes that agglutination was clearly observed. Further, the sign "±" denotes that it was difficult to determine whether or not agglutination occurred.

ter, an immunoactivity against the antigens was maintained while, in Comparative Example 12 where the antibody was combined with the excessive amount of the water-soluble coloring matter, the immunoactivity had lost.

Test Example 2 Difference in Color of Hair Dye

The hair dyes produced in Example 7 and Comparative Examples 11 and 12 were diluted so that each antibody concentration was the same as each other. Then, color differences among each hair dye was evaluated to represent the results in Table 2. In this table, the sign "−" denotes that no red color was observed while the sign "+" denotes that the red color was clearly observed Further, the sign "±" denotes that it was somewhat observed.

TABLE 2

|  | Difference in color |
| --- | --- |
| Example 7 | + |
| Comparative Example 11 | − |
| Comparative Example 12 | ± |

The hair dye in Comparative Example 11 was hardly red in spite of the fact that the hair dye was the same antibody concentration as that of the antibody in Example 7 where the red color was clearly recognized. Further, in Comparative Example 12 where the antibody was combined with the excessive amount of the water-soluble coloring matter, the immunoactivity against antigens had lost as shown in Table 1. Thus this hair dye of the Comparative Example 12 was not suitable.

Test Example 3 Hair Dye Test

The hair dyes produced in Examples 1–10 and Comparative Examples 1–12 were diluted with PBS containing 0.1% TWEEN 20 and 0.1% BSA, so that concentrations of the anti-hair antibody-immobilized coloring materials (=hair dyes) were all 0.1%. Then, in 1 ml of each hair dye was immersed a bundle of human grey hair (0.15 g), which was rotated at room temperature for 1 hour. Then, the hair bundle was washed while shook in physiological salt water con-

TABLE 1

|  | Examples | | | | | | | | | | Comparative Examples | | | | | | | | | | | |
| --- | --- | --- | --- | --- | --- | --- | --- | --- | --- | --- | --- | --- | --- | --- | --- | --- | --- | --- | --- | --- | --- | --- |
|  | 1 | 2 | 3 | 4 | 5 | 6 | 7 | 8 | 9 | 10 | 1 | 2 | 3 | 4 | 5 | 6 | 7 | 8 | 9 | 10 | 11 | 12 |
| Results of judgment | + | + | + | + | + | + | + | + | + | + | − | − | − | − | − | − | − | − | − | − | + | − |

In the hair dyes of Examples 1–12 on which antikeratin antibodies were immobilized, agglutination was observed to indicate that the immobilized antibodies maintained an immunoactivity against the antigens. In addition, it was found that, in Comparative Example 11 where the antibody was combined directly with the water-soluble coloring mattaining 0.02% TWEEN 20, and then was air-dried. The degree of coloring was visually evaluated. The sign ○ denotes that the hair has been colored, and the sign Δ denotes that the hair has been somewhat colored. The sign x represents that the hair has not been colored at all. The results are summarized in Table 3.

TABLE 3

| | Examples | | | | | | | | | | Comparative Examples | | | | | | | | | | | |
|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 1 | 2 | 3 | 4 | 5 | 6 | 7 | 8 | 9 | 10 | 11 | 12 |
| Results of coloring hairs | O | O | O | O | O | O | O | O | O | O | X | X | X | Δ | Δ | X | X | X | X | X | X | X |

As can be seen from Table 3, the grey hair was indeed colored with the hair dyes of Examples 1–10 where the anti-keratin antibodies were used. On the other hand, the hair was not sufficiently colored in Comparative Example 1–10 where the control antibody was used and also in Comparative Examples 11 and 12 where water-soluble coloring matter was directly combined with anti-keratin antibodies.

Test Example 4 Durability Test after Hair Dyeing

Using the hair dyes prepared in Examples 4, 5, 7, and 8, bundles of hair that had been colored in the same manner as in Test Example 3 underwent the following shampoo and brushing treatments. With these treatments, color durability was evaluated as follows.

(Shampoo Treatment)

Colored hair bundles were washed by hand in 10% aqueous solution of a commercially available shampoo, and then rinsed with running water followed by air-drying. The degree of coloring was visually evaluated.

(Brushing Treatment)

Colored hair bundles were brushed with a pig-hair brush, and the degree of coloring was visually evaluated.

The Results of each evaluation are represented in Table 4. It should be noted that only the shampoo treatment was applied with respect to hair dyes produced in Examples 4 and 5. In Table 4, an increasing number of the sign "+" indicates a higher degree of coloring. For the shampoo treatment, the first time application caused a slight color fading in hair dyes produced in Examples 4 and 5, but substantially no color fade was observed after the second time application, thus indicating that greater durability against shampoo treatment was demonstrated. In particular, hair dyes produced in Example 7 showed a high durability. For the brushing treatment, those hair dyes produced both in Examples 7 and 8 demonstrated a high durability.

TABLE 4

| | Number of repeats of shampoo treatment | | | | Number of repeats of brushing | | | |
|---|---|---|---|---|---|---|---|---|
| | 0 | 1 | 2 | 3 | 0 | 100 | 300 | 1000 |
| Example 4 | +++ | ++ | ++ | ++ | | | | |
| Example 5 | +++ | ++ | ++ | ++ | | | | |
| Example 7 | ++ | ++ | ++ | ++ | ++ | ++ | ++ | + |
| Example 8 | ++ | + | − | − | ++ | ++ | + | + |

Example 11 Anti-Keratin-immobilized Hair Dye

Water-insoluble polymethyl methacrylate latex (100 μm) to which a blue coloring matter had been adsorbed was combined with the anti-keratin antibodies of Example 1(2) in the same manner as in Example 2 to prepare hair dyes.

Example 12 Anti-Keratin-immobilized Blue Dextran Hair Dye 2 g of CIBACRON BLUE 3GA (Sigma, Inc.), and 1 g of DEXTRAN T-40 (molecular weight of 40,000, average molecular size of about 100 nm, water-soluble, produced by Pharmacia Co.) were dissolved in 90 ml of distilled water. Agitated at 60° C. for 30 minutes, then 9.88 g of sodium chloride was added and agitated at 60° C. for 1 hour. Temperature was raised to 80° C., and 0.875 g of sodium carbonate was added and agitated 80° C. for 2 hours. Unreacted CIBACRON BLUE was removed by gelfilter chromatography using Sephadex-25. Then, after oxidizing with sodium metaperiodate overnight, the solution thus obtained was subjected to dialysis against deionized water, and freeze-dried.

This freeze-dried CIBACRON BLUE-combined DEXTRAN T-40 was dissolved in a 20 mM boric acid buffer solution containing 0.14M sodium chloride to react with the anti-keratin antibody of Example 1(2) at 4° C. for 24 hours. Then, the resultant solution was reduced with hydrogenated sodium borate at 4° C. for 2 hours to obtain antibodies that had been immobilized on CIBACRON BLUE via dextran. On the hair dye thus obtained, it was found, 0.48 g of the CIBACRON BLUE per 1 g of dextran had been immobilized. In addition, about 0.5 g of the antibody per 1 g of dextran had been immobilized.

Comparative Example 13

Instead of the anti-keratin antibody produced in Example 12, the control antibody produced in Example 1(3) was immobilized on water-soluble blue dextran. This blue dextran was used to produce a hair dye which was designated as Comparative Example 13.

The hair dyes produced in Example 12 and Comparative Example 13 were diluted with PBS containing 0.1% TWEEN 20 and 0.1% BSA, so that concentrations of the antibody were 0.1 mg/ml. Then, into this solution was immersed a bundle of human grey hair at room temperature for a whole day and night. Then, the hair bundle was washed in physiological salt water containing 0.02% TWEEN 20. The degree of coloring was observed. As a result, it was found that, only in the case of Example 12, the grey hair had been colored. In this case it was demonstrated that this hair dye was resistent to color fading and that many functions such as tensity, resiliency, tautness, slipperiness, collectivity and tactile properties of hair had been improved.

Example 13 Anti-Keratin-immobilized Fluorescent Dextran Hair Dye (Preparation of Hair Dye)

DEXTRAN T-40 (water-soluble, produced by Pharmacia Co.) was oxidized with sodium metaperiodate for a whole day and night. After oxidation, the solution thus obtained was subjected to dialysis against deionized water to obtain oxidized dextran. An excessive amount of hexamethylene diamine was added to the oxidized dextran to react at 4° C. for 24 hours, followed by a reduction treatment with hydrogenated sodium borate at 4° C. for 2 hours. Unreacted hexamethylene diamine was removed by gel-filtration chromatography using Sephadex G-25 (produced by Pharmacia Co.) to obtain dextran to which amino groups had been introduced.

The afore-mentioned dextran to which amino group had been introduced and fluoresceine isothiocyanate (abbreviated as FITC hereinafter) (produced by Sigma Inc.) were reacted in a 0.5M carbonic acid buffer solution (pH 9.5) at 4° C. for 6 hours. Unreacted FITC was removed by gel-filter chromatography using Sephadex G-25, and then the solution was reacted with formaldehyde in the presence of hydrogenated sodium borate to block the remaining amino groups. The mixture was dialyzed against distilled water. Thus, dextran to which FITC had been introduced was obtained.

The afore-mentioned dextran to which FITC had been introduced was again oxidized with sodium metaperiodate. Then, the resultant solution was reacted to combine with amino groups of the anti-keratin antibodies produced in Example 1(2), thus obtaining antibodies that had been immobilized via dextran on FITC.

Comparative Example 14

The FITC-conjugated, water-soluble dextran without antibodies produced in Example 13 was designated as Comparative Example 14.

Comparative Example 15

Instead of the anti-keratin antibody produced in Example 13, the control antibody produced in Example 1(3) was immobilized on the dextran. The dextran thus obtained was designated as Comparative Example 15.

Comparative Example 16

To 2 ml of the anti-keratin antibody (10 mg/ml) produced in Example 1(2) and adjusted with PBS was added 0.2 ml of a 0.5M carbonic acid buffer solution (pH 9.5). Then, to the resultant solution was again added 0.2 ml of FITC (1.0 mg/ml) dissolved in the same buffer solution to react in the dark at 4° C. for 6 hours. After centrifugation, the reacted solution was applied to a Fast Desalting FPLC (available from Pharmacia Co.) equilibrated with a 0.005M PBS (pH 8.4) to remove unreacted FITC. DEAE Sepharose Fast Flow (available from Pharmacia Co.), was charged with about 5 ml of the resultant solution which was then washed with a 0.005M PBS (pH 8.4). The FITC-labeled conjugated antibodies adsorbed to the gel were eluted successively with a 0.005M PBS (pH 8.4)•(the first eluent), a 0.1M PBS (pH 6.4)•(the second eluent), and a 1.0M PBS (the third eluent) in this order. The third eluate fraction was collected and dialyed against physiological salt water. Thus, FITC-conjugated anti-keratin antibodies were obtained, and designated as Comparative Example 16.

Comparative Example 17

Instead of the anti-keratin antibody produced in Comparative Example 16, the control antibody produced in Example 1(3) wast conjugated with FITC, which was designated as Comparative Example 17.

Test Example 5 Evaluation of Binding Force to Hair

Bundles of hair colored in the same manner as in Test Example 3 using hair dyes produced in Examples 4 and and Comparative Example 16 were treated for one hour in eluents (1)–(4) shown in Table 5 and evaluated how the degreeof hair coloring would change. Visual observation was applied to hair dyes in Examples 4 and 7. On the other hand, a fluorescence microscope was used to observe hair colored with hair dyes in Comparative Examples 16

TABLE 5

| Eluents |
| --- |
| (1) 3M Sodium thiocyanate (pH 7.4) |
| (2) 6M guanidine HCl (pH 3) |
| (3) 8M urea (pH 7) |
| (4) 50% ethylene glycol (pH 11) |

The results of each evaluation are represented in Table 6. In Table 6, increasing number of the sign "+" indicates higher degree of coloring. Because of interaction between carbon black and hair, binding to hair in Example 4 was stronger than in Comparative Example 16, thus making its hair dye more resistant to color fading. In other words, it has been found that antibodies immobilized directly on inorganic pigments can bind more strongly with hair than antibodies immobilized directly on water-soluble coloring matter. Further, it has been found that even water-soluble coloring matter can be strongly bound to hair by immobilizing antibodies via water-insoluble macromolecular carriers on water-soluble coloring matter as evidenced in Example 7.

TABLE 6

| | Before elution | Eluents | | | |
| --- | --- | --- | --- | --- | --- |
| | | (1) | (2) | (3) | (4) |
| Example 4 | ++ | ++ | ++ | ++ | ++ |
| Example 7 | ++ | + | + | ++ | − |
| Comparative Example 16 | + | − | − | − | − |
| Example 7 | ++ | + | + | ++ | − |
| Comparative Example 16 | + | − | − | − | − |

Test Example 6 Sensuality Test after Hair Coloring

Sensuality tests were conducted on bundles of hair colored in the same manner as in Test Example 3 using hair dyes produced in Examples 4 and 7 and Comparative Example 16. 10 testing professionals judged how tensity, resiliency, tautness, slipperiness, collectivity and tactile properties of hair had changed over controls of hair bundles before coloring. The results of the judgment are shown in Table 7. Sensuality of the hair dyes of Examples 4 and 7 was improved as compared with that of Example 16. In particular, sensuality had been greatly improved in the hair dyes produced using colored latex in Example 7.

TABLE 7

| Test items | | Example 4 | Example 7 | Comparative Example 16 |
|---|---|---|---|---|
| Tensity | Number of testers responded positive | 6 | 10 | 6 |
| | Number of testers responded neutral | 4 | 0 | 4 |
| Resiliency | Number of testers responded positive | 7 | 9 | 3 |
| | Number of testers responded neutral | 3 | 1 | 7 |
| Tautness | Number of testers responded positive | 8 | 8 | 2 |
| | Number of testers responded neutral | 2 | 2 | 8 |
| Slipperiness | Number of testers responded positive | 7 | 6 | 4 |
| | Number of testers responded neutral | 3 | 4 | 6 |
| Collectivity | Number of testers responded positive | 5 | 7 | 2 |
| | Number of testers responded neutral | 5 | 3 | 8 |
| Tactile property | Number of testers responded positive | 6 | 7 | 2 |
| | Number of testers responded neutral | 4 | 3 | 8 | water containing 0.02% TWEEN 20. Fluorescent light was applied to colored hair to judge whether or not a difference was made in fluorescence strength between before and after coloring treatments. The results are presented in Table 8.

Test Example 8 Color Fading Test

The bundle of hair colored in Example 7 was washed with a commercially available shampoo. Fluorescent light was applied to the colored hair to judge whether or not a difference was made in fluorescence strength between before and after coloring treatments. Color fading was decided on the basis of the number of testing professionals who recognized the difference in fluorescence strength. The results are presented in Table 8.

Test Example 9 Sensuality Test

Professionals had judged how tensity, resiliency, tautness, slipperiness, collectivity and tactile properties of hair had changed as compared with hair bundles before coloring. The results are also presented in Table 8.

The judgment on each test in Examples 7 and 8 was made by 10 testing professionals.

TABLE 8

| | | | Example 13 | Comparative Example 14 | Comparative Example 15 | Comparative Example 16 | Comparative Example 17 |
|---|---|---|---|---|---|---|---|
| Test Example 7 (Coloring Test) | | Number of testers found difference in fluorescence | 10 | 3 | 3 | 4 | 1 |
| | | Number of testers found no difference in fluorescence | 0 | 7 | 7 | 6 | 9 |
| Test Example 8 (Color Fading Test) | | Number of testers found difference in fluorescence | 9 | 0 | 0 | 2 | 0 |
| | | Number of testers found no difference in fluorescence | 1 | 10 | 10 | 8 | 10 |
| Test Example 9 (Sensuality Test) | Dampishness | Number of testers responded positive | 9 | 2 | 1 | 2 | 10 |
| | | Number of testers responded neutral | 1 | 8 | 9 | 8 | 10 |
| | Smoothness | Number of testers responded positive | 8 | 1 | 3 | 2 | 2 |
| | | Number of testers responded neutral | 2 | 9 | 7 | 8 | 8 |
| | Suppleness | Number of testers responded positive | 8 | 0 | 1 | 2 | 1 |
| | | Number of testers responded neutral | 2 | 10 | 9 | 8 | 9 |
| | Slipperiness | Number of testers responded positive | 9 | 2 | 3 | 3 | 2 |
| | | Number of testers responded neutral | 1 | 8 | 7 | 7 | 8 |
| | Tactile property | Number of testers responded positive | 7 | 1 | 2 | 2 | 1 |
| | | Number of testers responded neutral | 3 | 9 | 8 | 8 | 9 |

Test Example 7 Dyeing Test

Into each hair dye produced in Example 13 and Comparative Examples 14–17 was immersed a bundle of human grey hair at room temperature for a whole day and night. Then, the hair bundle was washed with physiological salt Use of the hair dyes in Example 13 provided more fluorescent coloring matter bound to hair bundles compared with the hair dyes in Comparative Examples 14–17. It has been found that they are resistant to color fading associated with washing. In addition, use of such hair dyes improved tactile properties of hair itself.

Example 14 Rinse

The hair dye in Example 4 was formulated to prepare a rinse according to a method known in the art. The composition of the rinse having a coloring capability is shown in Table 9.

TABLE 9

|  | (% by weight) |
|---|---|
| Stearyl trimethyl ammonium chloride | 3.0 |
| Cetanol | 1.5 |
| Glycerine monostearate | 1.5 |
| 1,3-butylene glycol | 5.0 |
| Liquid paraffin | 2.0 |
| Perfume | proper quantity |
| Hair dye of Example 4 | 5.0 |
| Refined water | Balance |

The rinse thus prepared had been used continuously for one month. Evaluation covered coloring of grey hair, stains on faces and hands, color fading due to shampoo, itch and eruption of the scalp, and sensuality. As the results, the rinse prepared in Example 14 was found that it did color grey hair well without any stains on face or hand. No color fading was observed after shampooing. There was neither itch nor eruption on the scalp. The sensuality of the hair also had been improved.

Example 15 Rinse

The hair dye in Example 7 was formulated to prepare a rinse according to a method known in the art. The composition of the rinse having a coloring capability is shown in Table 10.

TABLE 10

|  | (% by weight) |
|---|---|
| Stearyl trimethyl ammonium chloride | 3.0 |
| Cetanol | 1.5 |
| Glycerine monostearate | 1.5 |
| 1,3-butylene glycol | 5.0 |
| Liquid paraffin | 2.0 |
| Perfume | proper quantity |
| Hair dye of Example 7 | 5.0 |
| Refined water | Balance |

The rinse thus prepared had been used continuously for one month. Evaluation covered coloring of grey hair, stains on faces and hands, color fading due to shampoo, itch and eruption of the scalp, and sensuality. As the results, the rinse prepared in Example 15 was found to dye well grey hair without any stains on face or hand. No color degradation was observed after shampooing. There was neither itch nor eruption on the scalp. The sensuality of the hair also had been improved. In addition, the same effects were recognized on those rinses that had been formulated with the hair dyes produced in Examples other than Examples 4 and 7.

Example 16 Rinse

The hair dye in Example 12 was formulated so as to have a composition shown in Table 11. Thus, a was obtained having a coloring capability.

TABLE 11

| Stearyl trimethyl ammonium chloride | 3.0 |
|---|---|
| Cetanol | 1.5 |
| Glycerine monostearate | 1.5 |
| 1,3-butylene glycol | 5.0 |
| Liquid paraffin | 2.0 |
| Perfume | proper quantity |
| Hair dye of Example 12 | 5.0 |
| Refined water | Balance to total 100 |

After shampooing, grey hair was treated with said rinse. As a result, the grey hair was colored so that they could not seen distinctively. Further, it was found that the rinse treatment could improve tactile properties of hair.

Example 17 Pretreatment with Alkali

A bundle of human white hair was treated in a 10% ammonia aqueous solution for 30 minutes while ultrasonic waves were applied. After treatment, the bundle was washed thoroughly with deionized water to obtain an alkali-pretreated hair bundle.

Example 18 Pretreatment with Surfactant

A bundle of human white hair was treated in a 1% SDS aqueous solution for an hour while ultrasonic waves were applied. After treatment, the bundle was washed thoroughly with deionized water to obtain an SDS-pretreated hair bundle.

Example 19 Pretreatment with L-Cystine

A bundle of human grey hair was treated in a 0.1M sodium carbonate buffer solution (pH 9) containing 0.2M L-cystine at 30° C. for 10 minutes. After treatment, the bundle was washed thoroughly with deionized water to obtain an L-cystine-pretreated hair bundle

Example 20 Pretreatment with Thioglycolic Acid

A bundle of human grey hair was treated in a 0.1 M sodium carbonate buffer solution (pH 9) containing 0.2M thioglycolic acid at 30° C. for 10 minutes. After treatment, the bundle was washed thoroughly with deionized water to obtain a thioglycolic acid-pretreated hair bundle

Example 21 Pretreatment and Hair Dyeing

The human grey hair pretreated in Examples 17–20 was colored with the hair dyes of Examples 2, 4 and 7 according to the method of Test Example 3.

Test Example 10 Coloring Efficiency Enhanced by Pretreatment

The hair dyed after the pretreatment in Example 21 was compared with the one dyed without any pretreatment. The results are shown in Table 12. It has been found that coloring efficiencies increased with pretreatment by means of alkali, SDS, L-cystine, and thioglycolic acid.

TABLE 12

| | Pretreatment agents for coloring antibody | | | | |
|---|---|---|---|---|---|
| Hair dyes | None | Example 17 | Example 18 | Example 19 | Example 20 |
| Example 2 | ○ | ⊙ | ⊙ | ⊙ | ⊙ |
| Example 4 | ○ | ⊙ | ⊙ | ⊙ | ⊙ |
| Example 7 | ○ | ⊙ | ⊙ | ⊙ | ⊙ |

Example 22 Shampoo

Thioglycolic acid as a pretreatment agent was compounded in a shampoo according to a method known in the art. The shampoo composition is shown in Table 13.

TABLE 13

| | (% by weight) |
|---|---|
| Polyoxyethylene lauryl ether sodium sulfate (2 E.O.) | 15.0 |
| Coconut oil fatty acid diethanolamide | 5.0 |
| Ethylene glycol distearate | 1.5 |
| Sodium benzoate | 0.2 |
| EDTA | 0.2 |
| Coloring matter | proper quantity |
| Perfume | proper quantity |
| Thioglycolic acid | 8.0 |
| Refined water | Balance |

Test Example 11 Coloring Efficiency Enhanced by Pretreatment (Practicality Test)

With the cooperation of 3 volunteers who had distinct grey hair, a half head test was conducted. That is, a half of the head was treated with the shampoo of Example 22 while the other half of the head was treated with a shampoo that had the same composition as that of Example 22 except for thioglycolic acid. They all used the hair dye-formulated rinse of Example 14.

As a result of one week's continuous use, grey hair, with the use of the shampoo of Example 22, was colored better than through the use of the other shampoo, and no grey hair had been distinctively seen on the former half head.

Example 23 Rabbit Anti-Bovine IgG Antibody-Immobilized Titan Black Hair Dye

A rabbit was immunized with bovine IgG, and a rabbit anti-bovine IgG antibody was obtained. According to the same method as in Example 2, the rabbit anti-bovine IgG antibody was immobilized on Titan Black. This rabbit anti-bovine IgG antibody-immobilized Titan Black was demonstrated to bind specifically to bovine IgG in such a agglutination test as conducted in Test Example 1.

Example 24 Multi-step Dyeing

A bundle of human white hair, which had been colored with a hair dye composed of anti-keratin antibody-immobilized Titan Black (Example 2), was again colored with a hair dye composed of the rabbit anti-bovine IgG antibody-immobilized Titan Black that had been produced in Example 23, according to the same method as in Test Example 3.

Test Example 12 Coloring Efficiency Enhanced by Multi-step Dyeing

As a result of the additional coloring in Example 24, it has been indicated that the human grey hair, which had been colored with a hair dye comprising anti-keratin antibody-immobilized Titan Black, could be further richly colored as illustrated in Table 14. In the table, an increasing number of the sign "+" indicates a higher degree of coloring.

Example 25 Rabbit Anti-Bovine IgG Antibody-Immobilized Carbon Black Hair Dye According to the same method as in Example 5, the rabbit anti-bovine IgG antibody was immobilized on carbon black. This rabbit anti-bovine IgG antibody-immobilized carbon black was demonstrated to bind specifically to bovine IgG in such a agglutination test as conducted in Test Example 1.

Example 26 Multi-step Dyeing

A bundle of human grey hair, which had been colored with a hair dye comprising anti-keratin antibody-immobilized carbon black (Example 5), was again colored with a hair dye composed of the rabbit anti-bovine IgG antibody-immobilized carbon black that had been produced in Example 25, according to the same method as in Test Example 3.

Test Example 13 Coloring Efficiency Enhanced by Multi-step Dyeing

As a result of the multi-step dyeing in Example 26, it has been indicated that the human grey hair, which had been colored with a hair dye comprising anti-keratin antibody-immobilized carbon black, could be further richly colored as illustrated in Table 14.

Example 27 Rabbit Anti-Bovine IgG Antibody-Immobilized Red Latex Hair Dye

According to the same method as in Example 7, the rabbit anti-bovine IgG antibody was immobilized on red latex (water-insoluble). This rabbit anti-bovine IgG antibody-immobilized carbon black was demonstrated to bind specifically to bovine IgG in such a agglutination test as conducted in Test Example 1.

Example 28 Multi-step Dyeing

A bundle of human grey hair, which had been colored with a hair dye comprising anti-keratin antibody-immobilized red latex (Example 7), was again colored with a hair dye comprising the rabbit anti-bovine IgG antibody-immobilized red latex that had been produced in Example 27, according to the same method as in Test Example 3.

Test Example 14 Coloring Efficiency Enhanced by Multi-step Dyeing

As a result of the multi-step dyeing in Example 28, it has been indicated that the bundle of human grey hair, which had been colored with a hair dye comprising anti-keratin antibody-immobilized red latex, could be further richly colored as illustrated in Table 14.

Example 29 Rabbit Anti-Bovine IgG Antibody-Immobilized Black Latex Hair Dye

According to the same method as in Example 9, the rabbit anti-bovine IgG antibody was immobilized on black latex (water-insoluble). This rabbit anti-bovine IgG antibody-immobilized carbon black was demonstrated to bind specifically to bovine IgG in such a agglutination test as conducted in Test Example 1.

Example 30 Multi-step Dyeing

A bundle of human grey hair, which had been colored with a hair dye comprising anti-keratin antibody-immobilized black latex (Example 9), was again colored with a hair dye comprising the rabbit anti-bovine IgG antibody-immobilized black latex that had been produced in Example 27, according to the same method as in Test Example 3.

Test Example 15 Coloring Efficiency Enhanced by Multi-step Dyeing

As a result of the multi-step dyeing in Example 30, it has been indicated that the bundle of human grey hair, which had been colored with a hair dye comprising anti-keratin antibody-immobilized black latex, could be further richly colored as illustrated in Table 14.

Example 31 Rabbit Anti-Bovine IgG Antibody-Immobilized Blue Dextran Hair Dye According to the same method as in Example 12, the rabbit anti-bovine IgG antibody was immobilized to blue dextran

Example 32 Multi-step Dyeing

A bundle of human grey hair, which had been colored with a hair dye comprising anti-keratin antibody-immobilized blue dextran (Example 12), was again colored with a hair dye comprising the rabbit anti-bovine IgG antibody-immobilized blue dextran that had been produced in Example 31, according to the same method as in Example 12.

Test Example 16 Coloring Efficiency Enhanced by Multi-step Dyeing

As a result of the multi-step dyeing in Example 32, it has been indicated that the bundle of human grey hair, which had been colored with a hair dye comprising anti-keratin antibody-immobilized blue dextran, could be further richly colored as illustrated in Table 14. Thus, it has been demonstrated that plural repetitive dyeing treatments were effective in order to increase the degree of coloring the hair that had been already colored in Example 12.

TABLE 14

| Primary Hair Dye | Secondary Hair Dye | Degree of coloring |
| --- | --- | --- |
| Example 2 | Example 23 | +++ |
| Example 2 | — | ++ |
| Example 5 | Example 25 | +++ |
| Example 5 | — | ++ |
| Example 7 | Example 27 | +++ |
| Example 7 | — | ++ |
| Example 9 | Example 29 | +++ |
| Example 9 | — | ++ |
| Example 12 | Example 31 | ++ |
| Example 12 | — | + |

Examples 33 and 34 Multi-step Dyeing

A bundle of human grey hair that had been colored with a hair dye comprising anti-keratin antibody-immobilized Titan Black (Example 2), and a bundle of human grey hair that had been colored with a hair dye comprising anti-keratin antibody-immobilized carbon black (Example 5), were each colored again with a hair dye comprising the rabbit anti-bovine IgG antibody-immobilized carbon black that had been produced in Example 25 and a hair dye comprising the rabbit anti-bovine IgG antibody-immobilized Titan Black that had been produced in Example 23, receptively, according to the same method as in Test Example 3.

Test Example 17 Change in Coloring Efficiency and Hue by Multi-step Dyeing

As a result of the multi-step dyeing in Examples 32 and 34, it has been indicated that the bundle of human grey hair, which had been colored with a hair dye comprising anti-keratin antibody-immobilized Titan Black, could not only be further richly colored with a hair dye comprising rabbit anti-bovine IgGa antibody-immobilized carbon black, but also the hue of the dyed or colored hair turned from bluish black to reddish black as illustrated in Table 15. In the table, the increasing number of the sign "+" indicates a higher degree of coloring. In addition, the bundle of human grey hair, which had been colored with a hair dye comprising anti-keratin antibody-immobilized carbon black, could not only be further richly colored with a hair dye comprising rabbit anti-bovine IgG antibody-immobilized Titan Black, but also the hue of the dyed or colored hair turned from reddish black to bluish black as illustrated in Table 15. Thus, it has been demonstrated that repeated colorings were effective in order to increase the degree of coloring of the hair that had been already colored in Example 12.

TABLE 15

| Example | Primary Hair Dye | Secondary Hair Dye | Degree of coloring | Hue |
| --- | --- | --- | --- | --- |
| 33 | Example 2 | Example 25 | +++ | Reddish black |
|  | Example 2 | — | ++ | Bluish black |
| 34 | Example 5 | Example 23 | +++ | Bluish black |
|  | Example 5 | — | ++ | Reddish black |

Example 35 Rinse

The hair dye in Example 23 was compounded in a rinse according to a method known in the art. The composition of the rinse having a coloring capability is shown in Table 16.

TABLE 16

|  | (% by weight) |
| --- | --- |
| Stearyl trimethyl ammonium chloride | 3.0 |
| Cetanol | 1.5 |
| Glycerine monostearate | 1.5 |
| 1,3-butylene glycol | 5.0 |
| Liquid paraffin | 2.0 |
| Perfume | proper quantity |
| Hair dye of Example 23 | 5.0 |
| Refined water | Balance |

Example 36 Rinse

The hair dye in Example 25 was compounded in a rinse according to a method known in the art. The composition of the rinse having a coloring capability is shown in Table 17.

TABLE 17

|  | (% by weight) |
| --- | --- |
| Stearyl trimethyl ammonium chloride | 3.0 |
| Cetanol | 1.5 |
| Glycerine monostearate | 1.5 |
| 1,3-butylene glycol | 5.0 |
| Liquid paraffin | 2.0 |
| Perfume | proper quantity |
| Hair dye of Example 25 | 5.0 |
| Refined water | Balance |

Example 37 Rinse

The hair dye in Example 27 was compounded in a rinse according to a method known in the art. The composition of the rinse having a coloring capability is shown in Table 18.

TABLE 18

|  | (% by weight) |
| --- | --- |
| Stearyl trimethyl ammonium chloride | 3.0 |
| Cetanol | 1.5 |
| Glycerine monostearate | 1.5 |
| 1,3-butylene glycol | 5.0 |
| Liquid paraffin | 2.0 |
| Perfume | proper quantity |
| Hair dye of Example 27 | 5.0 |
| Refined water | Balance |

Example 38 Multi-step Dyeing

After grey hair had been colored for a while with the rinse comprising the hair dye produced in Example 14, other rinses comprising the hair dyes produced in Examples 35,36, or 37 were applied.

Test Example 18 Coloring Efficiency Enhanced by Multi-step Dyeing

As a result of the multi-step dyeing in Example 38, it has been indicated that the rinse produced in Examples 35,36, or 37 could further increase the degree of coloring. In the case of the rinse produced in Example 35, the hue of the dyed or colored grey hair turned from reddish black to bluish black.

INDUSTRIAL APPLICABILITY

The present invention provides hair dyes that are excellent in coloring capability, are resistant to color fading, do not stain skin because of their specific affinity to hair, do not irritate skin, and increase tactile properties of hair as well.

Further, in the case of hair cosmetics or hair care products containing conventional hair dyes, such hair dyes do not possess a specific affinity to hair, and sometimes cause skin eruption, not to mention skin stains. Thus, because of these disadvantages, it has been impossible to increase hair dye contents, thus requiring the repetition of hair dyeing operation. In contrast therewith, the hair dye of this invention has an affinity specific to hair so that the hair dyes can be added to hair cosmetics or hair care products in sufficiently high concentration. In addition, the hair dye of this invention can be adapted for wide application in a variety of hair cosmetics or hair care products. Thus, there are practical and outstanding advantages such that, without providing negative effects on the scalp, daily use of such hair cosmetics of the present invention can maintain beautiful color, gloss, touch and tactile properties of hair.

We claim:

1. A hair coloring composition comprising an antibody having an immunoactivity against hair and a coloring material, wherein said antibody is immobilized on said coloring material, said coloring material is a composite of a macromolecular carrier and a coloring substance selected from the group consisting of dyes and pigments, and the substance-constituting unit size of said coloring material is at least equivalent to that of said antibody.

2. A hair coloring composition as claimed in claim 1, wherein said coloring substance is water-insoluble and a weight ratio of the antibody to the coloring substance ranges 1:5–1:100.

3. A hair coloring composition as claimed in claim 2, wherein said water-insoluble coloring substance is an inorganic pigment.

4. A hair coloring composition as claimed in claim 1, wherein a weight ratio of the macromolecular carrier to the coloring substance in said composite ranges 1:0.001–1:10.

5. A hair coloring composition as claimed in claim 4, wherein said macromolecular carrier is water-insoluble.

6. A hair coloring composition as claimed in claim 5, wherein said water-insoluble macromolecular carrier is composed of particulates having an average particle diameter ranging 0.001–100 μm, and 0.01–100 mg of said antibody are supported on 1 g of said macromolecular carrier.

7. A hair coloring composition as claimed in claim 6, wherein said water-insoluble macromolecular carrier has an average particle diameter ranging from 0.001–1 μm.

8. A hair coloring composition as claimed in claim 7, wherein said water-insoluble macromolecular carrier has an average particle diameter ranging 0.05–0.7 μm.

9. A hair coloring composition as claimed in claim 4, wherein said water-insoluble macromolecular carrier is at least one compound selected from the group consisting of water-insoluble polysaccharides, derivatives thereof, water-insoluble proteins, derivatives thereof, synthetic polymers and liposomes.

10. A hair coloring composition as claimed in claim 9, wherein said synthetic polymers are at least one polymer having reactive groups selected from the group consisting of polystyrene, polychlorostyrene, polychloromethyl styrene, polyacrylic acid, polymethacrylic acid, polymaleic acid, polystyrene sulfonic acid, poly ( 2-acrylamide-2-methylpropane sulfonic acid), poly[N-2 -hydroxypropyl) methacrylamide], poly(2-hydroxyethyl methacrylate), poly(glycerol monomethacrylate), poly(2-oxyethyl acrylate), poly(2-oxyethyl methacrylate), polyethyleneglycol methacrylate, copolymers thereof; and those polymers that have been provided with reactive groups by means of surface reforming.

11. A hair coloring composition as claimed in claim 9, wherein said water-insoluble polysaccharides and derivatives thereof, and water-insoluble proteins comprise at least one compound selected from the group consisting of cross-linked, insolublized compounds and polymers of agarose, dextran, chitin, fibroin, gelatin and collagen.

12. A hair coloring composition as claimed in claim 4, wherein said macromolecular carrier is water-soluble.

13. A hair coloring composition as claimed in claim 12, wherein said water-soluble macromolecular carrier comprises at least one polymeric compound selected from the group consisting of polysaccharides, proteins, derivatives thereof and synthetic polymers.

14. A hair coloring composition as claimed in claim 12, wherein said water-soluble macromolecular carrier has a number-averaged molecular weight of 10,000–2,000,000, and 0.01–1,000 mg of the antibody are supported on 1 g of said macromolecular carrier.

15. A hair coloring composition as claimed in claim 1, wherein said coloring material is composed of a coloring substance having an average particle diameter of 0.01–6 μm.

16. A method of coloring hair, which comprises: treating hair with a pretreatment agent for hair dye antibodies, said pretreatment agent containing at least one chemical substance selected from the group consisting of reducing agents, surfactants, alkaline substances and enzymes; and then contacting the hair with the coloring composition of claim 1.

17. A method of coloring hair, which comprises: contacting the hair with a hair coloring composition according to claim 1 followed by contacting the hair with a hair dye comprising a coloring material on which a secondary antibody having an immunoactivity against said anti-hair antibodies has been immobilized.

18. A method of coloring hair which comprises: treating hair with a pretreatment agent for hair dye antibodies, containing at least one chemical substance selected from the group consisting of reducing agents, surfactants, alkaline substances and enzymes; and then contacting the hair with the hair coloring composition according to claim 1 followed by contacting the hair with a dyeing agent comprising a coloring material on which a secondary antibody having an immunoactivity against said anti-hair antibody has been immobilized.

19. A hair coloring composition as claimed in claim 13, wherein said water-soluble macromolecular carrier has a number-averaged molecular weight of 10,000–2,000,000, and 0.01–1,000 mg of the antibody are supported on 1 g of said macromolecular carrier.

20. A hair coloring composition comprising a coloring material and a secondary antibody having an immunoactivity against a first antibody having an immunoactivity against hair , wherein said secondary antibody is immobilized on said coloring material, said coloring material is a composite of a macromolecular carrier and a coloring substance selected from the group consisting of dyes and pigments, and the substance-constituting unit size of said coloring material is at least equivalent to that of said secondary antibody.

21. A hair coloring composition as claimed in claim 20, wherein said macromolecular carrier is water-soluble.

* * * * *

UNITED STATES PATENT AND TRADEMARK OFFICE
CERTIFICATE OF CORRECTION

PATENT NO. : 5,597,386
DATED : January 28, 1997
INVENTOR(S) : Shigeru Igarashi, et al It is certified that error appears in the above-indentified patent and that said Letters Patent is hereby corrected as shown below:

On the title page, item [54], in the title "COMPOSITION" to ---COMPOSITIONS---.

IN THE CLAIMS:

Column 34, line 33; after "ranging" insert ---from---.

Column 34, line 51; change "reform-" to ---modification---.
         line 52; delete "ing".

Column 35, line 16; after "claim 1" insert ---,---.

Column 36, line 1; after "claim 1" insert ---,---.

Signed and Sealed this

Nineteenth Day of August, 1997

Attest:

BRUCE LEHMAN

*Attesting Officer*    *Commissioner of Patents and Trademarks*